US00PP30187P2

(12) United States Plant Patent
Higgins

(10) Patent No.: US PP30,187 P2
(45) Date of Patent: Feb. 12, 2019

(54) ***MANDEVILLA* PLANT NAMED 'SUNPAVARIAKA'**

(50) Latin Name: *Mandevilla hybrida*
Varietal Denomination: Sunpavariaka

(71) Applicant: T. Jay Higgins, Sarasota, FL (US)

(72) Inventor: T. Jay Higgins, Sarasota, FL (US)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/732,932

(22) Filed: Jan. 12, 2018

(51) Int. Cl.
*A01H 5/00* (2018.01)

(52) U.S. Cl.
USPC ..... Plt./232
CPC ..... *A01H 5/00* (2013.01)

(58) Field of Classification Search
USPC ..... Plt./232
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Mandevilla* plant named 'Sunpavariaka', characterized by its vining plant habit; vigorous growth habit; freely branching habit; variegated leaves; early flowering habit; long flowering period; and numerous red-colored flowers.

1 Drawing Sheet

Botanical designation: *Mandevilla hybrida.*
Cultivar denomination: 'SUNPAVARIAKA'.

BACKGROUND OF THE INVENTION

The present invention relates to a new and distinct cultivar of *Mandevilla* plant, botanically known as *Mandevilla hybrida* and hereinafter referred to by the name 'Sunpavariaka'.

The new *Mandevilla* plant is a naturally-occurring branch mutation of *Mandevilla hybrida* 'Sunmandecrikin', disclosed in U.S. Plant Pat. No. 17,736. The new *Mandevilla* plant was discovered and selected by the Inventor on a single flowering plant of the proprietary selection in a controlled nursery environment in Sarasota, Fla. in May, 2015.

Asexual reproduction of the new *Mandevilla* plant by terminal vegetative cuttings in Sarasota, Fla. since October, 2015 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpavariaka'. These characteristics in combination distinguish 'Sunpavariaka' as a new and distinct *Mandevilla* plant:

1. Vining plant habit.
2. Vigorous growth habit.
3. Freely branching habit.
4. Variegated leaves.

5. Early flowering habit.
6. Long flowering period.
7. Numerous red-colored flowers.

Plants of the new *Mandevilla* can be compared to plants of the mutation parent, 'Sunmandecrikin'. Plants of the new *Mandevilla* differ primarily from plants of 'Sunmandecrikin' in the following characteristics:

1. Plants of the new *Mandevilla* have smaller leaves than plants of 'Sunmandecrikin'.
2. Plants of the new *Mandevilla* and 'Sunmandecrikin' differ in leaf color as plants of 'Sunmandecrikin' have variegated leaves.
3. Plants of the new *Mandevilla* have smaller flowers than plants of 'Sunmandecrikin'.

Plants of the new *Mandevilla* can be compared to plants of the *Mandevilla splendens* 'FGRRV1', disclosed in U.S. Plant Pat. No. 28,446. In side-by-side comparisons, plants of the new *Mandevilla* differ from plants of 'FGRRV1' in the following characteristics:

1. Leaves of plants of the new *Mandevilla* are lanceolate in shape whereas leaves of plants of 'FGRRV1' are elliptic to ovate in shape.
2. Plants of the new *Mandevilla* and 'FGRRV1' differ in leaf color as plants of 'FGRRV1' have medium green and creamy white variegated leaves.
3. Plants of the new *Mandevilla* and 'FGRRV1' differ in flower color as plants of 'FGRRV1' have red purple-flowers with yellow-colored flower throats.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpavariaka' grown in a container.

The photograph at the bottom of the sheet is a close-up view of a typical flowering plant of 'Sunpavariaka'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpavariaka'.

Parentage: Naturally-occurring branch mutation of *Mandevilla hybrida* 'Sunmandecrikin', disclosed in U.S. Plant Pat. No. 17,736.

Propagation:

*Type*.—By terminal vegetative cuttings.

*Time to initiate roots*.—About two weeks at temperatures about 23° C. to 25° C.

*Time to produce a rooted young plant*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Vining plant habit; vigorous growth habit; freely branching habit.

*Plant height* (*with support*).—About 90 cm.

*Lateral branch description*.—Length: About 10 cm. Diameter: About 3.5 mm. Internode length: About 2.7 cm. Strength: Strong, flexible. Texture: Pubescent, rough. Color, developing: Close to 144A; faint spots, close to N199B; apices, close to N199A. Color, fully developed: Close to 199B.

Leaf description:

*Arrangement*.—Opposite, simple.

*Length*.—About 8.6 cm.

*Width*.—About 2.8 cm.

*Shape*.—Lanceolate.

*Apex*.—Acuminate.

*Base*.—Cordate.

*Margin*.—Entire; slightly undulate.

*Texture and luster, upper and lower surfaces*.—Pubescent, rough.

*Venation pattern*.—Pinnate, reticulate.

*Color*.—Developing leaves, upper surface: Close to 144A; towards the margins, close to 162D. Developing leaves, lower surface: Close to 146B; towards the margins, close to 162D. Fully expanded leaves, upper surface: Close to NN137B; towards the margins, close to 162D; venation, close to 145C. Fully expanded leaves, lower surface: Close to NN137D; towards the margins, close to 161D; venation, close to 145C.

*Petioles*.—Length: About 8.9 cm. Diameter: About 1.8 mm. Texture, upper and lower surfaces: Smooth, glabrous. Color, upper and lower surfaces: Close to 144B.

Flower description:

*Flower type and habit*.—Single salverform flowers arranged in axillary racemes; flowers face mostly upright to outwardly; freely flowering habit with about three to five flowers per inflorescence and about 60 flowers developing per plant.

*Natural flowering season*.—Early flowering habit, plants begin flowering about six weeks after planting; long flowering period, plants flower continuously from summer until late autumn in Japan.

*Flower longevity on the plant*.—About seven to ten days; flowers not persistent.

*Fragrance*.—None detected.

*Flower buds*.—Height: About 6.6 cm. Diameter: About 1.3 cm. Shape: Trullate. Color: Distally, close to 70C; proximally, close to 149D tinged with close to 58C.

*Flowers*.—Appearance: Salverform; flared trumpet, corolla fused and five-parted; flowers roughly star-shaped. Diameter: About 7.7 cm. Depth (length): About 6.8 cm. Throat diameter: About 1.7 cm. Tube length: About 2.9 cm. Tube diameter, proximally: About 3.7 mm.

*Corolla*.—Quantity and arrangement: Five petals arranged in a single whorl and fused towards the base into an elongated tube; petal lobes separate and not imbricate. Petal lobe length: About 2.9 cm. Petal lobe width: About 2.5 cm. Petal lobe shape: Obovate, strongly asymmetrical. Petal lobe apex: Acute. Petal lobe margin: Entire; slightly recurved and undulate. Petal lobe texture and luster, upper surface: Smooth, glabrous; matte. Petal lobe texture and luster, lower surface: Smooth, glabrous; glossy. Throat texture and luster: Smooth, glabrous; matte. Tube texture and luster: Smooth, glabrous; matte. Color: Petal lobe, when opening, upper surface: Close to between 46B and 53B; towards the margins, close to 53C. Petal lobe, when opening, lower surface: Close to 51B. Petal lobe, fully opened, upper surface: Close to 53B to 53C; at the edges, flushed with close to 54C; venation, close to 53A; color becoming closer to 53B to 53D and subsequently close to 54A with development. Petal lobe, fully opened, lower surface: Close to 54B and N57D. Throat: Distally, close to 53A; proximally, close to 15A; venation, close to 149D. Tube: Distally, close to 55B; proximally, close to 68B; venation, close to 150D tinged with close to 54B.

*Calyx*.—Quantity and arrangement: Five sepals arranged in a single whorl, fused at the base; calyx, star-shaped. Sepal length: About 3 mm. Sepal width: About 1.9 mm. Sepal shape: Lanceolate. Sepal apex: Acuminate. Sepal margin: Entire. Sepal texture, upper and lower surfaces: Smooth, glabrous. Sepal color, upper surface: Close to 145D. Sepal color, lower surface: Close to 145D; towards the apex, tinged with close to 35D.

*Peduncles*.—Length: About 5.3 cm. Diameter: About 2.4 mm. Texture: Smooth, glabrous. Aspect: Mostly outwardly. Color: Close to 146A.

*Pedicels*.—Length: About 1.7 cm. Diameter: About 2.3 mm. Texture: Smooth, glabrous. Aspect: Upright to outwardly. Color: Close to 146C slightly overlain with close to 180B.

*Reproductive organs*.—Stamens: Quantity and arrangement: Typically five; filaments fused to corolla; anthers, connivent. Anther size: About 1.6 mm by 6.8 mm. Anther shape: Lanceolate. Anther color: Close to 162B. Pollen amount: Scarce. Pollen color: Close to 162B. Pistils: Quantity: Typically one. Pistil length: About 1.9 cm. Style color: Close to 145C. Stigma shape: Globose. Stigma color: Close to 145B. Ovary color: Close to 145A.

*Seeds and fruits*.—Seed and fruit production have not been observed on plants of the new *Mandevilla* to date.

Pathogen & pest resistance: Plants of the new *Mandevilla* have not been noted to be resistant to pathogens and pests common to *Mandevilla* plants to date.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpavariaka' as illustrated and described.

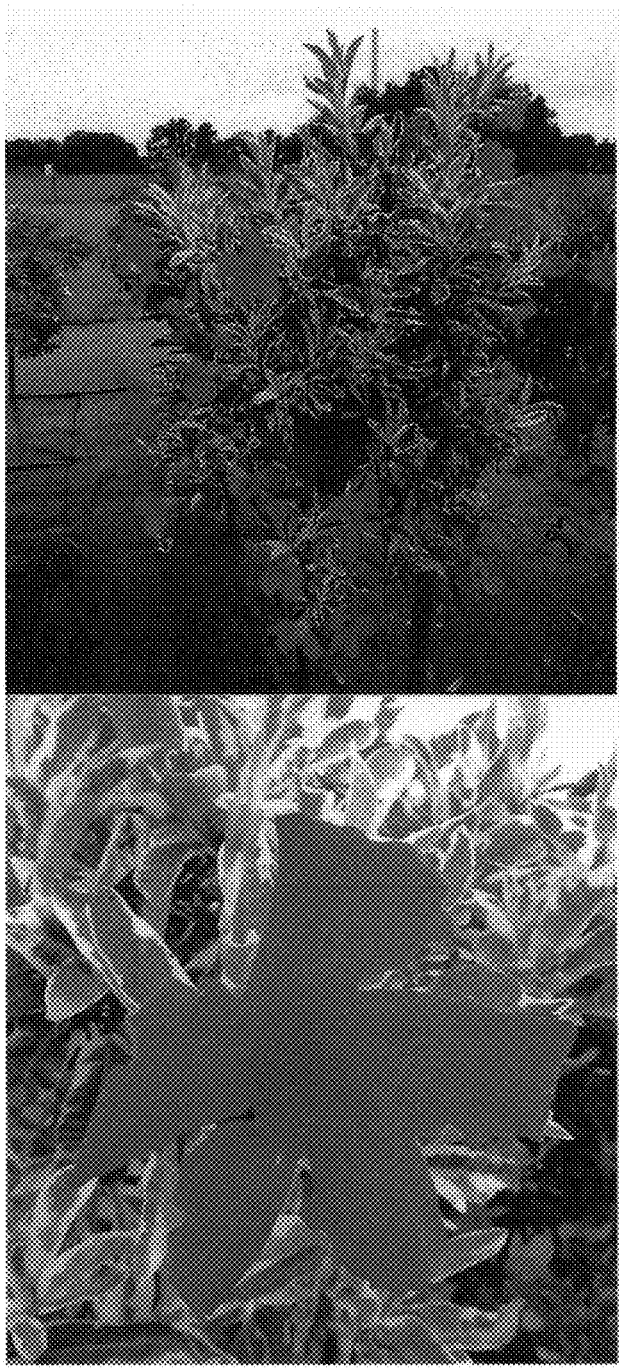

* * * * *